(12) United States Patent
Van Heugten

(10) Patent No.: US 6,736,510 B1
(45) Date of Patent: May 18, 2004

(54) OPHTHALMIC TALBOT-MOIRE WAVEFRONT SENSOR

(75) Inventor: Anthony Van Heugten, Sarasota, FL (US)

(73) Assignee: Ware Tec Vision Systems, Inc., Pacific Palisades, CA (US)

( * ) Notice: Subject to any disclaimer, the term of this patent is extended or adjusted under 35 U.S.C. 154(b) by 0 days.

(21) Appl. No.: 10/357,980

(22) Filed: Feb. 4, 2003

(51) Int. Cl.$^7$ .................................................. A61B 3/10
(52) U.S. Cl. ...................................................... 351/221
(58) Field of Search ................................. 351/205, 206, 351/211, 212, 221, 209, 210, 246, 204, 216, 213

(56) References Cited

U.S. PATENT DOCUMENTS

| | | | |
|---|---|---|---|
| 5,164,750 A | * 11/1992 | Adachi | 351/212 |
| 5,949,521 A | 9/1999 | Williams et al. | |
| 5,963,300 A | * 10/1999 | Horwitz | 351/209 |
| 5,994,687 A | 11/1999 | Chanteloup et al. | |
| 6,007,204 A | 12/1999 | Fahrenkrug et al. | |
| 6,043,885 A | 3/2000 | Mazuet et al. | |
| 6,050,687 A | 4/2000 | Loesel | |
| 6,095,651 A | 8/2000 | Williams et al. | |
| 6,155,684 A | 12/2000 | Bille et al. | |
| 6,199,986 B1 | 3/2001 | Williams et al. | |
| 6,270,221 B1 | 8/2001 | Liang et al. | |
| 6,409,345 B1 | 6/2002 | Molebny et al. | |

FOREIGN PATENT DOCUMENTS

WO    WO92/01417    2/1992

\* cited by examiner

*Primary Examiner*—George Manuel
(74) *Attorney, Agent, or Firm*—Sanford Astor

(57) ABSTRACT

A system for measuring the eye comprising a light source 10 which sends a narrow collimated beam of light 12, to reflect from a beam splitter 14. The beam of light 12 enters the eye 16 through the pupil 17 where it is focused to a point 20 on the retina 18. The light 12 is reflected from the retina 18 where it passes through a series of relay lenses 22, 24. The light then passes through one or more reticles 26, 28. A CCD camera 30 records the shadow pattern formed by reticles 26, 28. The shadow pattern is digitized into a computer and algorithms are created to calculate the distortions. As a result of the above steps being performed, the refractive power of the eye can be measured at many points, simultaneously.

30 Claims, 1 Drawing Sheet

OPHTHALMIC TALBOT-MOIRE WAVEFRONT SENSOR

BACKGROUND OF THE INVENTION

Improving eyesight is vitally important. Precise measurement of the eye's physical characteristics, including features of the eye, in order to prescribe vision correction is also vitally important.

With the advent of new technologies capable of creating more complex optical surfaces, a resurgence of interest has arisen in the tools required to measure the eye's optical characteristics to a higher degree of complexity than was possible before.

This invention is an improvement on a system described by U.S. Pat. No. 5,963,300 to Horwitz. In the Horwitz system, a light beam is projected into the eye. The light beam is of a diameter equal to or larger than that of the eye's pupil. The eye focuses the light beam onto the retina, the beam then reflects back out of the eye, through the optical components of the eye. A relay lens system collects the light reflected from the eye, projecting the collected light through a reticle, or a plurality of reticles. A spatial filter (an iris), is positioned within the relay lens system to block unwanted reflected light. The light that passes through the reticle(s), is projected onto a translucent screen to create a image on the screen. A charged coupled device CCD camera is focused onto the screen to "see" the patterns created by the reticle(s). A computer is used to convert the CCD camera images to digital data. The computer then analyzes the data to determine the refractive condition of the eye. The computer also analyzes the position of the reflected glint from the vertex of the cornea as well as the position of the pupil, compares the two positions, and determines where the eye is gazing.

There are several methods available to measure the reflected wavefront of an eye. The method of this invention is known as "Talbot/Moire Interferometry." Of the other methods available, the most common method is known as a "lenslet array system",or a "Hartmann Shack" sensor. Such a wavefront sensor is described by Liang et al. in "Objective Measurement of Wave Aberrations of the Human Eye with the Use of a Hartmann-Shack Wave-Front Sensor," Journal of the Optical Society of America, Vol. 1, No. 7, July 1994, p.p 1949–1957.

One of the earlier Hartmann Shack systems is described by U.S. Pat. No. 5,949,521 to Williams. A light beam is projected into the eye. Williams first passes the light through optical components and then reflects it from a deformable mirror before projecting it into the eye. A relay lens system collects the light reflected from the eye, projecting the collected light onto a deformable mirror, which in turn reflects it to a lenslet array.

A lenslet array is a disc with many, many tiny lenses, much like an insect eye, but flat instead of spherical. The lenslet array creates numerous spots of light focused into aerial images. If the light being collected by a tiny lens approaches the lens "straight on",then the spot that the tiny lens forms will be along the optical axis of the tiny lens. However, if the light is approaching the tiny lens not "straight on", but skewed off to one side of the optical axis, then the resulting spot will be formed to one side of the optical axis of the tiny lens. When the reflected light emerging from an eye being analyzed is not perfectly aligned along the optical axis, then the eye has a defect in it. The resulting shift in the position of the spot formed by the tiny lens indicates the type of, and the degree of the defect in the eye. The positions of each of the tiny lenses are related to the optical performance of the corresponding position of the eye. In other words, a tiny lens at the very top of the array that is collecting light emerging from the eye will produce a spot, and subsequent information about the light that emerged from the top of the eye. Conversely, a spot on the bottom of the array corresponds to the bottom of the eye, and so forth. (If the image is inverted or mirrored, as it sometimes is depending upon the optical design, then the relationship must be adjusted accordingly. For example, if the image is inverted, then the "top" of the eye will be represented by a spot on the "bottom" of the array.) A CCD camera is focused onto the aerial plane where the spots come into focus, "seeing" the spots of light. A computer is used to convert the CCD camera images to digital data. The computer then analyzes the data to determine the refractive condition of the eye, by comparing the shift of each spot from where the spot would have been had the eye been defect free. The computer changes the shape of the deformable mirror to alter the resulting spot pattern produced by the lenslet array, attempting to alter it in such a manner to bring the spots closer to the position where the spots would have been for a properly focusing eye.

An improvement on the Hartmann Shack system is described by U.S. Pat. No. 6,270,221 to Liang et al. Liang et al had difficulty relying upon the human eye to focus the incoming large light beam into a small spot on the retina, due to the shortcomings of the Hartmann Shack lenslet system. The very thing that made the Hartmann Shack device useful (measuring eyes with problems focusing), gave it trouble with those eyes. Eyes that did not focus well could not be measured because the reflected wavefront did- not originate from a small spot, it originated from a large spot, degrading the performance of the lenslets. Because the Hartmann Shack system uses lenslets, it is very sensitive to this type of error. The Liang et al solution was to add focusing lenses to converge or diverge the illumination beam to compensate for the refractive deficiencies of the eye, as well as the extreme sensitivity of the Hartmann Shack lenslet system to this problem.

BRIEF DESCRIPTION OF THE INVENTION

Applicant's invention is an improvement on the Horwitz system.

With respect to Horwitz, the light beam projected into the eye, in Applicant's system, is of a diameter much less than the diameter of the eye's pupil. The Horwitz system required that the eye's cornea and lens focus the light into a small point on the surface of the retina. When a patient's eye was working well, a small point of light did form on the retina. However, if a patient's eye was not working well, or was simply accommodating, a small point of light was not formed. Instead, a larger spot of light was formed. The worse the refractive condition of the eye, the larger the spot became. This resulted in light being reflected from the retina from many points, which degraded the image quality of the fringes. The addition of a spatial filter and screen helped filter out many of the unwanted reflections, but not all. More importantly though, the spatial filter placed a limit on the :measurement range of the device, and the screen reduced its sensitivity to some higher order aberrations. Reduced sensitivity to these higher order aberrations may have been acceptable, and even desirable at the time of the Horwitz invention, but now it is desirable to measure and quantify them. Additionally, the measurement range of the previous device was acceptable in its time, but now higher measurement range demands are being placed on these systems, and more range is required.

By using a beam diameter much smaller than the eye's pupil diameter, such as less than 1 mm, the beam passes through the central axis of the eye, where virtually no refraction takes place. Regardless of the optical performance of the patient's eye, or its accommodative state, the light still forms into a small spot on the retina, which results in a much better quality return signal for purposes of fringe pattern generation. Small illumination beam diameters may also be projected into the eye from other angles and positions, so long as they impinge upon the retina at the point corresponding to the central optical axis.

No topography or pachymetry is employed. Applicant's invention only analyzes the light reflected from the retina and refracted through all the optical components of the eye. It does not analyze light reflected from other surfaces such as the cornea and crystalline lens. No eye tracking is performed. Unlike the Horwitz system, no spatial filter or screen is used.

With respect to the Williams system, Applicant's invention does not use a deformable mirror to modify the light being projected into the eye, nor does it use a deformable mirror to modify the reflected light being collected from the eye. Deformable mirrors are quite complex, adding significant cost to the Williams system. Applicant's system is simpler, lower in cost, more robust and simpler to service and maintain. Applicant's system does not use a lenslet array. It utilizes instead a reticle, a completely different optical method than the lenslet array. The lenslet array condenses and converts the wavefront into spots, whereas the reticle preserves the wavefront and images it by introducing contrasting dark and light lines within it. The Williams' spots indicate the wavefront shape, whereas Applicant's dark lines indicate the wavefront shape. As a result, Applicant's system can measure both fine, medium and coarse aberrations, whereas the Williams system can only measure medium aberrations. Two limitations of the Hartmann-Shack (HS) aberrometer required by Williams are: measuring coarse aberrations and measuring fine aberrations. Williams' underlying assumption is that the wavefront is locally flat, and each lenslet cleanly focuses the collected light into a small spot. The position of this spot is then measured as to how far it deviates from the lenslet's optical axis, and a determination can then be made as to the error in the wavefront being collected. This assumption breaks down when the lenslet collects light that has coarse aberrations because the light cannot be focused. into a small spot. Significant curvature of the wavefront causes a blurry spot, making it difficult to measure the position of the spot's central location. This assumption again breaks down when the lenslet collects light that has fine aberrations because again, the light cannot be focused into a small spot.

Also as a result of using a lenslet array, the Williams' system cannot see the eye being evaluated within the image that the lenslet array produces, it can only see an approximate position. Williams requires a second camera to see the eye being evaluated, not only adding complexity, but introducing potential measurement error. Applicant's system can see the eye within the image produced by the reticle(s). This not only results in a simpler system because only one camera is required, it also guarantees that the wavefront measurement is accurately matched to the location of the pupil.

Because of the use of a lenslet array, Williams cannot accurately locate the glint (purkinje image) within the image that the lenslet array produces, but Applicant's system can see the glint within its image. The observation of, and the accurate identification of the location of this point of light is essential in ensuring that the patient's eye being measured is gazing directly into the wavefront measurement device. Gaze angle misalignment will result in the inadvertent incorrect measurement of the optical center of the eye. The resulting corrective action being taken on the eye, surgery or corrective lenses, will produce the extremely undesired result of the correction being de-centered.

A further advantage of using reticle(s) rather than lenslet arrays is that more robust means (Fourier Analysis), can be used to analyze the signal, making the system not only less susceptible to signal loss, but more reliable in the mathematical calculations. One of the reasons for this advantage is that Applicant's invention is not required to locate the central spot of each single image formed by each single lenslet. Instead the image is converted into the frequency domain, allowing far more opportunities for the application of mathematical analysis algorithms, described in greater detail later in the specification.

With respect to Liang et al, Applicant's invention not only differs significantly in that no lenslet array is used, but it also does not use focusing means to condition the illumination beam. In addition to the aforementioned problems of using lenset arrays, using such focusing means adds complexity and cost to the system, as well as adding time to make the measurement because of the added steps required to adjust the incoming beam to match the properties of the patient's eye.

OBJECTS OF THE INVENTION

It is an object of the present invention to provide a system which will measure aberrations in the eye to determine the prescription required to correct for defects.

It is also an object of the invention to use two devices simultaneously to provide a system to allow the investigation of both eyes simultaneously.

It is a further object of the invention to provide a system to measure the eye which can be connected to a device to make Intraocular Lenses (IOLs), contact lenses or custom spectacle lenses.

It is yet a further object of the invention to provide a system to measure the eye which can be connected to a device to guide Laser Surgery.

Yet another object of the invention is to provide a system to measure aberrations with the patient's glasses or contacts on, to test/screen if the prescription is correct.

Still another object of the invention is provide a system to measure the focus of non-verbal children, with and without glasses; measure for IOL prescriptions once a human lens is out of the bag, but before an artificial IOL is inserted and to measure refraction as the IOL is being tuned in the eye.

These and other objects of the invention will be seen from the detailed description of the invention that follows.

DETAILED DESCRIPTION OF THE INVENTION

Figure 1:
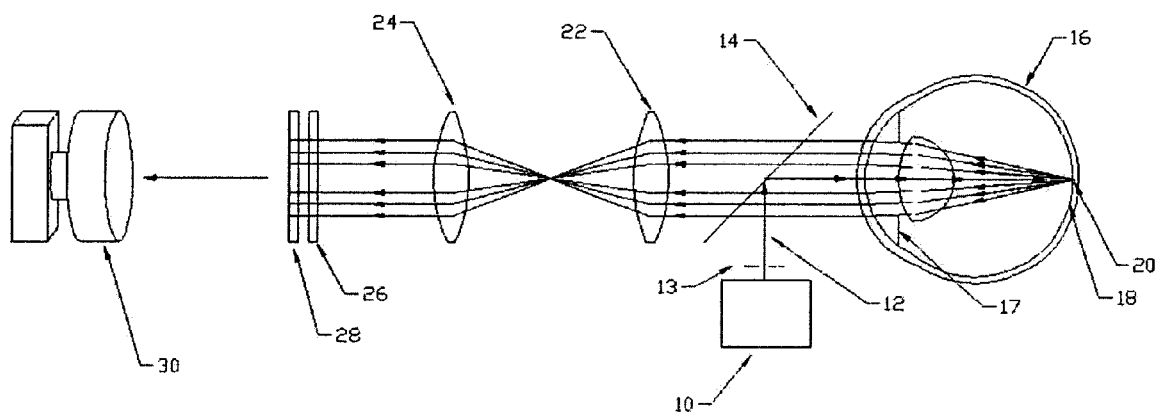
FIG. 1 is a schematic diagram of the system in accordance with the present invention.

FIG. 1 schematically shows the ocular biometer of this invention. A light source, such as a laser 10 sends a narrow collimated beam of light 12, less than the diameter of the pupil of the eye, usually less than about 1 mm in diameter, to reflect from a beam splitter 14. The beam of light 12 enters the eye 16 through the pupil 17 where it is focused to a point 20 on the retina 18.

If the diameter of beam of light 12 is required to be smaller than the standard output of the laser being used, then aperture 13 is placed in front of the laser to reduce its size. In the preferred embodiment, the aperture is made from a thin sheet of non-reflective plastic with a hole of the desired beam diameter drilled through the center, but other materials may be used, as well as other shapes, such as a conical shape on the side of the laser, and/or a conical shape in the hole, to direct to an acceptable place any undesired light that may reflect from the aperture material.

The light is reflected from the retina 18 where it passes through a series of relay lenses 22, 24. The light then passes through one or more reticles 26, 28.

A CCD (charge coupled device) camera 30 records the shadow pattern formed by reticles 26, 28, or by reticle 26 alone, if only one reticle is used. The shadow pattern is digitized into a computer and algorithms are created to calculate the distortions. As a result of the above steps being performed, the refractive power of the eye can be measured at many points across the pupil, simultaneously.

In the preferred embodiment, light source 10 is producing light of a wavelength of 770 to 790 nm (nanometers), preferably 780 nm. Although the device will function with many other wavelengths, this particular wavelength of light is optimum for today's available camera technology, the human eye's lack of aversion to it and the eye's ability to refract this wavelength in the similar way that it refracts light in the visible spectrum.

Today's commonly available CCD cameras are quite sensitive to this wavelength, reducing the required amount of light that is needed to obtain a good return signal from the eye. Less light is better due to safety issues. Although there are cameras available that are sensitive to these longer wavelengths, their cost is substantially higher. It is expected that in the future, these higher wavelength sensitive cameras will become more commonly available and at a lower cost.

The human eye's pupil will close when the eye senses that more light is entering the eye than is needed for seeing. The amount of light that is projected into the eye in order for the device to function is more than the eye needs to see. At a wavelength shorter than 780 nm, the eye would sense it, and close the pupil. This is undesirable because the device will only measure the wavefront that escapes from the pupil, and full pupil opening is required for proper measurement. Therefore, by using 770–790 nm wavelength, a constant beam of light can be projected into the eye during the positioning of the patient, avoiding the complexities of flashing a light and capturing an image in the brief time that it takes for the eye's pupil to respond.

The light 12 produced must also be highly collimated, ideally to less than 15 arc seconds of divergence or convergence. This quality of collimation helps create a smaller point of light on the retina, resulting in a better return signal.

Beam splitter 14, in its preferred embodiment, has a transmission/reflectance of 90/10. Although 90 percent of the light produced by the light source has passed through the beam splitter and lost, this is required to minimize the amount of light to be projected into the eye. This is because the light that is reflected from the eye must also pass through the beam splitter, and a portion of this light will also be reflected. For example, if a light source produces 100 units of light, and the beam splitter reflects 10 percent, then 10 units of light will be projected into the eye. In this example, assume that 50% is reflected out from the eye, or, 5 units of light. As the 5 units of reflected light pass through the beam splitter on the return path out of the eye, 10 percent, or 0.5 units are reflected, leaving 4.5 units of light to pass through and illuminate the reticle 26. However, if the beam splitter were 50/50, it would be required to project 18 units of light, 80% more, into the eye to obtain the same 4.5 units available to illuminate the reticle (18 units into the eye, 9 units reflected out, 4.5 reflected by the 50/50 beamsplitter, 4.5 transmitted to the reticle). Although the light being produced is then less (36 units versus 100), and less is wasted (18 versus 90), the amount of light projected into the eye is increased by 80%. Less light projected into the eye is safer than more light projected into it. Although it is preferred to use this arrangement of beam splitter ratio, the device will work with almost any other ratio as well, except that the light level to the eye will be reduced or increased.

Relay lenses 22 and 24 are made from two pieces of glass each, cemented together (known as achromats). This configuration allows for a better focus of the image onto the reticle.

It is also preferred to use two relay lenses of identical focal lengths. In such a configuration the image projected onto the reticle is of an almost identical size as the pupil being imaged. Other focal length variations are possible, and in some applications desireable due to space limitation, but when done, the image size shift must be allowed for in the calculations of the analysis.

Reticle 26, and reticle 28 in those instances when more than one reticle is used, are crossed gratings. The gratings are solid lines etched onto a glass substrate, with one set of parallel lines intersecting the other set of parallel lines at 90 degrees. The period between the lines is 25.4 micrometers, but other period distances may also be used. In the preferred embodiment, the lines are solid, with distinct edges, but sinusoidal lines may also be used. Between each line is a clear line, of equivalent width to the solid or sinusoidal line.

The light that is reflected from the eye is referred to as the "wavefront." If an eye has no defects in its optical performance, the wavefront will be flat. If the eye has defects in its optical performance, the wavefront will deviate from a flat shape. The amount of and the shape of this deviation in the wavefront will indicate the amount of and the type of refractive errors in the eye being studied. After the wavefront has passed through the first reticle, an aerial image is formed of the wavefront at a plane beyond the reticle. The image reforms again and again at subsequent repeating planes beyond the reticle. This is known as the "Talbot Effect." Depending upon the wavelength of light used, and the spacing period of the gratings, the Talbot planes are predictable as to where they will form and reform. When the CCD camera 30 focuses on these aerial images, the wavefront can be seen as a series of dark and light lines. The dark and light lines are distorted proportionately to the distortion of the wavefront passing through the reticle.

Adding a second reticle at one of the Talbot planes, and slightly rotating it with respect to the first reticle creates a "Moire Effect." The Moire Effect amplifies, or exaggerates the distortion of the dark and light lines, creating Fringes. These Fringes are more easily discernable by the camera. This places less resolution demands upon the camera. This also allows a wider field of view to be used without having to use an exotic, super-high resolution camera. The dark and light lines are referred to herein as "fringes" regardless of whether they are formed by the Talbot or the Moire effect.

Camera 30 is comprised of a focusing lens to gather the light in the image that forms at one of the Talbot planes, which focuses the image of the Fringes onto a CCD chip. A CCD camera is used because the wavelength of light used is invisible to the human eye, so fringes will also be invisible. Other camera types, such as film cameras, may also be used, but the time required to process the film makes the process slow and costly. The use of a CCD camera provides many images, instantly, without processing cost. Other types of electronic cameras are available, but the CCD camera is preferred because of its dimensional stability, robustness, sensitivity to low light, and low cost.

The image of the fringes can then be analyzed in a number of methods, but the preferred method is to digitize the image into a computer and create algorithms to calculate the fringe distortions. A reference image is created of fringes resulting from a flat wavefront, then compared to the fringes created by the patient's eye. Any change in position of a fringe from the reference image can be construed as a refractive change in the point of the eye being measured at the corresponding point in the fringe. In other words, a fringe at the top :center of the image represents the refractive power of the eye in the top center of the pupil (unless the image is inverted or mirrored, in which case compensating reassignments of location are performed).

There are many algorithmic approaches to measure the fringes to determine the refractive power of the eye, but the simplest method is used in this disclosure. Those skilled in the art of mathematical analysis may employ more complex algorithms, but these more complex algorithms would be based upon the following foundation:

At any Region of Interest (ROI), the position of the fringe in the resulting image is measured and compared to the corresponding position of the fringe in the reference image. The positions are expressed in terms of their X and Y coordinates, and a delta X and Y is calculated by subtracting the X and Y positional values of the resultant fringe from the X and Y position of the reference fringe. The change in position of the fringe is proportional to the amount of refractive change in that ROI, relative to the refractive power in the reference image at that same corresponding ROI. Also, within the boundaries of the fringes can be sub-fringes, which may be analyzed to a greater level of detail than the fringe within which these sub-fringes may be found.

The ratio of the amount of movement of fringes to the amount of refractive power change is determined by performing an analysis of the system's response to various known refractive elements placed in the system, and measured. Those skilled in the art of optics and mathematics may be able to calculate this predicted change in fringe position to refractive power ratio without the need for actual measurement, but the preferred method is to actually measure the system response using calibrated lenses to allow for any deviation from the design specifications that may have occurred in the system during fabrication.

The preferred method of mathematical analysis is to convert the image of the fringes from the visual domain to the frequency domain. This is accomplished using a Fast Fourier Transform, a mathematical routine known to those skilled in the art of mathematical analysis of machine vision images. The resulting multi-dimensional array of frequencies can then be analyzed using conventional programs such as "IDL", (available from Kodak Corporation, Rochester, N.Y.), and the algorithms developed can then be converted into most any standard computer programming language such as "C" language.

An example of such analysis is as follows:

The fringe image is converted into the Frequency Domain by using a standard Fast Fourier Analysis. The resulting image of the frequencies will produce five dominant points. The central point is discarded as noise, and the four remaining dominant points are identified. The positional shift of the dominant points can then be translated directly into defocus and astigmatism. Through testing with commonly available lenses of known optical properties, the positional movement of the dominant points can be easily understood and predicted for that particular systems's optical design configuration. An example of one such movement pattern would be a purely rotational movement of all four points to indicate defocus, and a movement of only two of the four points to indicate astigmatism. The shape change of the dominant points indicates higher order aberrations of the eye, and such shape changes can again be easily understood and predicted for that particular system's optical design configuration through testing with commonly available lenses with known optical properties. An example of one such shape change would be an elongation of the dominant points about the central axis of the Fast Fourier Transform array to indicate spherical aberration.

Once the refractive power of the eye is measured at many points, a power map of the eye is created. This map is comprised of the X Y coordinates of each ROI, and its corresponding refractive power. This power map may then be used as a diagnostic tool to quantify the eye's refractive performance. The test may be performed with or without the patient wearing corrective lenses. If they are wearing corrective lenses, the power map represents the power of the eye and the power of the corrective lens combined.

The information produced by the system may be attached to other devices which correct or improve vision either by modifying the eye itself, or fabricating a lens to be used with, on, or in the eye. These devices can be laser surgery lasers, eye cornea reshaping lasers and mechanisms, or corrective lens making machines such as spectacle lenses, contact lenses, or lenses to be implanted in the eye. All of these devices are referred to as "Corrector Devices."

In order for the system of this invention to be connected to a Corrector Device to correct or improve vision, the information produced from the power map must be further processed and conditioned. The first step in the processing is to calculate the refractive change required. This is done by subtracting the actual refractive power at each ROI from the desired refractive power at the same ROI. A new power map is then created which shows the correction required. This new power map must then be converted into a format understood by the Corrector Device(s) that will perform the task of changing the eye or making the corrective lens.

Although there are numerous formats of data used in Corrector Devices, and in many cases different devices use different formats, the foundation upon which all conclusions are made as to what the device will do is based upon the requirements dictated by the desired refractive power that the eye must end with. Although those skilled in the art may be able to devise different data formats, a very common means of expressing refractive power requirements for such Corrective Devices are Zernike Coefficients, or "Zernikes."

Zernikes may also be calculated by different methods, known to those skilled in the art. In the preferred method, the slope of the change in refractive power is expressed for both X and Y directions across the eye. The values are input into a commercially available program "IDL" (available from Kodak Corporation, Rochester, N.Y.) and a subroutine is written to convert the slope values into Zernikes, using mathematical concepts known to those skilled in the art of optics and mathematics.

Once the Zernikes are produced, they are piped directly to the Corrective Device, which then can perform its function. Details of Zernike Polynomials are disclosed in the reference, "Standards of Reporting the Optical Aberrations of Eyes" Thibos et al, OSA Optics Net.

As a result of the above steps being performed, the refractive power of the eye can be measured at many, many points across the pupil, simultaneously. In addition, two devices may be used simultaneously to investigate and measure both eyes simultaneously.

Having thus described the invention, the invention is to be considered limited only by the following claims.

I claim:

1. A system for measuring characteristics of the eye comprising:
   (a) means for generating an optical wavefront, the diameter of the wavefront being less than the diameter of the pupil of the eye being measured;
   (b) means to transmit the optical wavefront to the eye, the wavefront reflecting from a point on the retina of the eye;
   (c) means to transmit the reflected wavefront from the eye to reticle means;
   (d) one or more reticle means through which the reflected optical wave front is passed to create a shadow pattern;
   (e) means for analyzing the shadow pattern to produce measurement data of the characteristics of the wavefront, thereby providing measurement characteristics of the eye.

2. The system of claim 1 wherein the optical wavefront is a collimated beam of light less than about 1 millimeter in diameter.

3. The system of claim 1 further comprising means for generating a collimated beam of a predetermined wavelength to generate the optical wavefront.

4. The system of claim 3 further comprising means to generate a collimated beam with a wavelength of from 770 to 790 nanometers.

5. The system of claim 4 further comprising means to generate a collimated beam with a wavelength of about 780 nanometers.

6. The system of claim 1 in which the means to transmit the reflected wavefront from the eye is a series of relay lenses.

7. The system of claim 6 in which the relay lenses are achromats.

8. The system of claim 1 in which the means to analyze the shadow pattern is a CCD camera which records the shadow patterns, which are digitized into a computer for analysis.

9. The system of claim 2 in which the collimated beam of light is less than 15 arc seconds of divergence or convergence.

10. The system of claim 7 comprising two relay lenses of equal focal length.

11. The system of claim 1 comprising a first reticle and a second reticle rotated with respect to the first reticle, creating a moiré effect.

12. The system of claim 1 in which the measurement characteristics of the eye are transferred to an eye corrective device.

13. The system of claim 12 in which the corrective device is a laser surgery laser, eye cornea reshaping laser, or a corrective lens producing device.

14. The system of claim 12 in which the measurement characteristics of the eye are converted to Zernikes, prior to transfer to a corrective device.

15. A system for measuring characteristics of the eye comprising:
   (a) a light source for generating an optical wavefront, the diameter of the wavefront being less than the diameter of the pupil of the eye being measured;
   (b) a beam splitter to transmit the optical wavefront to the eye, the wavefront reflecting from a point on the retina of the eye;
   (c) relay lenses to transmit the reflected wavefront from the eye to one or more reticles through which the reflected optical wavefront is passed to create a shadow pattern;
   (d) a camera to record the shadow pattern;
   (e) digitizing the recorded shadow pattern into a computer;
   (f) analyzing the digitized shadow pattern to produce measurement data of the characteristics of the wavefront, thereby providing measurement characteristics of the eye.

16. The system of claim 15 wherein the optical wavefront is a collimated beam of light less than about 1 millimeter in diameter.

17. The system of claim 15 further comprising means for generating a collimated beam of a predetermined wavelength to generate the optical wavefront.

18. The system of claim 17 further comprising means to generate a collimated beam with a wavelength of from 770 to 790 nanometers.

19. The system of claim 18 further comprising means to generate a collimated beam with a wavelength of about 780 nanometers.

20. The system of claim 15 in which the relay lenses are achromats.

21. The system of claim 16 in which the collimated beam of light is less than 15 arc seconds of divergence or convergence.

22. The system of claim 15 comprising two relay lenses of equal focal length.

23. The system of claim 15 comprising a first reticle and a second reticle rotated with respect to the first reticle, creating a moiré effect.

24. The system of claim 15 in which the measurement characteristics of the eye are transferred to an eye corrective device.

25. The system of claim 24 in which the corrective device is a laser surgery laser, eye cornea reshaping laser, or a corrective lens producing device.

26. The system of claim 24 in which the measurement characteristics of the eye are converted to Zernikes, prior to transfer to a corrective device.

27. The system of claim 15 in which the camera is a CCD camera.

28. A system for measuring characteristics of the eye comprising:
   (a) a light source for generating an optical wavefront comprising a collimated beam of light less than the diameter of the eye being measured, said collimated beam of light having a wavelength of about 780 nanometers;
   (b) a beam splitter to transmit the optical wavefront to the eye, the wavefront reflecting from a point on the retina of the eye;
   (c) two achromat relay lenses of equal focal length to transmit the reflected wavefront from the eye to a first reticle and a second reticle rotated with respect to the first reticle, creating a moiré effect;

(d) a CCD camera to record the moiré effect;

(g) digitizing the recorded moiré effect into a computer;

(h) analyzing the digitized moiré effect to produce measurement data of the characteristics of the wavefront, thereby providing measurement characteristics of the eye.

29. The system of claim 1, 15 or 28 further comprising aperture means to narrow the diameter of the beam of light to less than the diameter of the pupil of the eye being measured.

30. The system of claim 1, 15 or 28 further comprising two systems used simultaneously, to measure both eyes simultaneously.

* * * * *

UNITED STATES PATENT AND TRADEMARK OFFICE
CERTIFICATE OF CORRECTION

PATENT NO. : 6,736,510 B1
DATED : May 18, 2004
INVENTOR(S) : Anthony Van Heugten It is certified that error appears in the above-identified patent and that said Letters Patent is hereby corrected as shown below:

<u>Title page,</u>
Item [73], Assignee, should read -- Wave Tec Vision Systems, Inc. --.

Signed and Sealed this

Second Day of May, 2006

JON W. DUDAS
*Director of the United States Patent and Trademark Office*

UNITED STATES PATENT AND TRADEMARK OFFICE
CERTIFICATE OF CORRECTION

PATENT NO. : 6,736,510 B1
APPLICATION NO. : 10/357980
DATED : May 18, 2004
INVENTOR(S) : Anthony Van Heugten It is certified that error appears in the above-identified patent and that said Letters Patent is hereby corrected as shown below:

<u>Title page,</u>
Item [73], Assignee, should read -- WaveTec Vision Systems, Inc. --.

This certificate supersedes the Certificate of Correction issued May 2, 2006.

Signed and Sealed this

Second Day of December, 2008

JON W. DUDAS
*Director of the United States Patent and Trademark Office*